United States Patent [19]

Goans et al.

[11] 4,080,960
[45] Mar. 28, 1978

[54] ULTRASONIC TECHNIQUE FOR CHARACTERIZING SKIN BURNS

[75] Inventors: Ronald E. Goans; John H. Cantrell, Jr., both of Knoxville, Tenn.; F. Bradford Meyers, East Alton, Ill.; Harry D. Stambaugh, Louisville, Ky.

[73] Assignee: The United States of America as represented by the United States Department of Energy, Washington, D.C.

[21] Appl. No.: 738,982

[22] Filed: Nov. 4, 1976

[51] Int. Cl.² ............................................. A61B 10/00
[52] U.S. Cl. .................................................. 128/2 V
[58] Field of Search ................ 128/2 V, 2.05 Z, 24 A

[56] References Cited

U.S. PATENT DOCUMENTS

| 3,269,173 | 8/1966 | Von Ardenne | 128/2 V |
| 3,830,223 | 8/1974 | Beretsky et al. | 128/2 V |

OTHER PUBLICATIONS

Stouffer, J. R. et al., *Proc. of 14th Ann. Sci. Conf. of Amer. Inst. of Ultrasound in Med.*, Oct. 1969, 1 page.

*Primary Examiner*—Kyle L. Howell
*Attorney, Agent, or Firm*—Dean E. Carlson; Stephen D. Hamel; Fred O. Lewis

[57] ABSTRACT

This invention, a method for ultrasonically determining the depth of a skin burn, is based on the finding that the acoustical impedance of burned tissue differs sufficiently from that of live tissue to permit ultrasonic detection of the interface between the burn and the underlying unburned tissue. The method is simple, rapid, and accurate. As compared with conventional practice, it provides the important advantage of permitting much earlier determination of whether a burn is of the first, second, or third degree. In the case of severe burns, the usual two - to three-week delay before surgery may be reduced to about 3 days or less.

10 Claims, 6 Drawing Figures

ULTRASONIC TECHNIQUE FOR CHARACTERIZING SKIN BURNS

BACKGROUND OF THE INVENTION

This invention was made in the course of, or under, a contract with the United States Energy Research and Development Administration. The invention relates generally to methods for characterizing skin burns with respect to depth and more particularly to an improved method for objectively measuring burn depth and therefore burn severity.

Skin burns are traditionally categorized as first degree, second degree, and third degree. First-degree burns involve damage only to the epidermis, or outermost layer of the skin. Second-degree burns extend into and terminate in the layer of skin next below—i.e., the dermis. Third-degree burns extend through both the epidermis and dermis and into the underlying layer of subcutaneous fat.

Early and accurate determination of the depth of a non-superficial burn is essential for prompt evaluation of its severity and an early decision as to the best mode of treatment. For example, the increasingly preferred treatment for all third-degree burns and deep dermal burns is excision to the depth of tissue destruction, followed by skin grafting. Unfortunately, conventional techniques do not lend themselves to prompt and accurate determination of burn depth. Thus, it is common in the case of severe burns to defer the desired excision and skin-grafting until after the dead tissue separates spontaneously. This often involves a delay of from 3 to 4 weeks. Thus, a relatively rapid and accurate method for determining burn depth should reduce mortality and lead to a more effective, rapid and complete rehabilitation for the patient. It would also reduce the time expended by the burn surgeon.

Conventional techniques for measuring the depth of a skin burn include analysis with infrared; measurement of the skin temperature; staining with dyes to delineate the burn-to-tissue interface; and pricking the burn surface to determine sensation. In general, these techniques are deficient from the standpoints of reliability and accuracy.

SUMMARY OF THE INVENTION

This invention may be summarized as follows: the method of determining the depth of a skin burn in animal tissue, said method comprising: acoustically coupling an electric-to-acoustic transducer to the surface of said burn through an intervening layer of a coupling medium whose acoustical impedance approximates that of said tissue; electrically exciting the transducer to (a) transmit ultrasonic pulses having a peak frequency in the range of about 0.5 to 40 megahertz inwardly through said burn and (b) generate, from resulting reflected ultrasonic waves electrical signals separated by a time interval proportional to the distance between the coupling-medium-to-burn-surface interface and the burn-to-unburned-tissue interface; and determining the depth of said burn from said signals.

Figure 2:
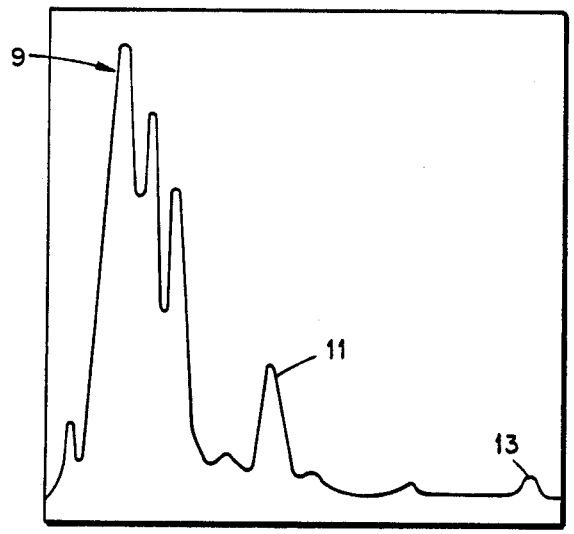
FIG. 2 is an idealized representation of an ultrasonic reflection spectrum of a burn in animal tissue, the spectrum being produced in accordance with this invention.
Figure 3:
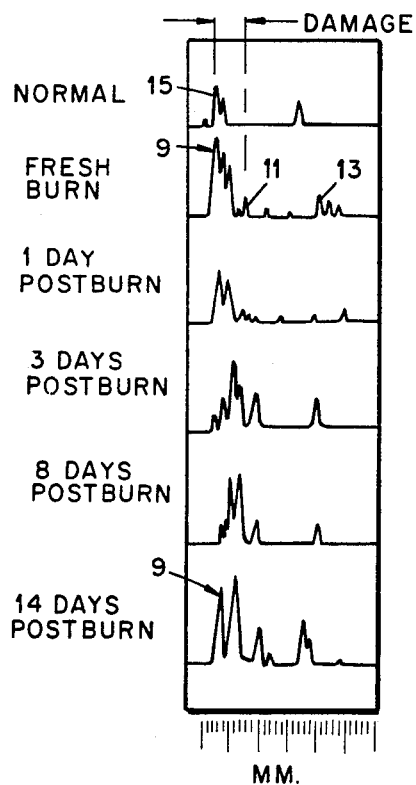
FIG. 3 is a series of drawings depicting ultrasonic reflection spectra obtained from a control sample of porcine tissue and a burn in corresponding tissue of the same animal, and FIG. 4 consists of FIGS. 4A and 4B, which are drawings of ultrasonic reflection spectra obtained from a human patient having a thigh burn.
Figure 4:
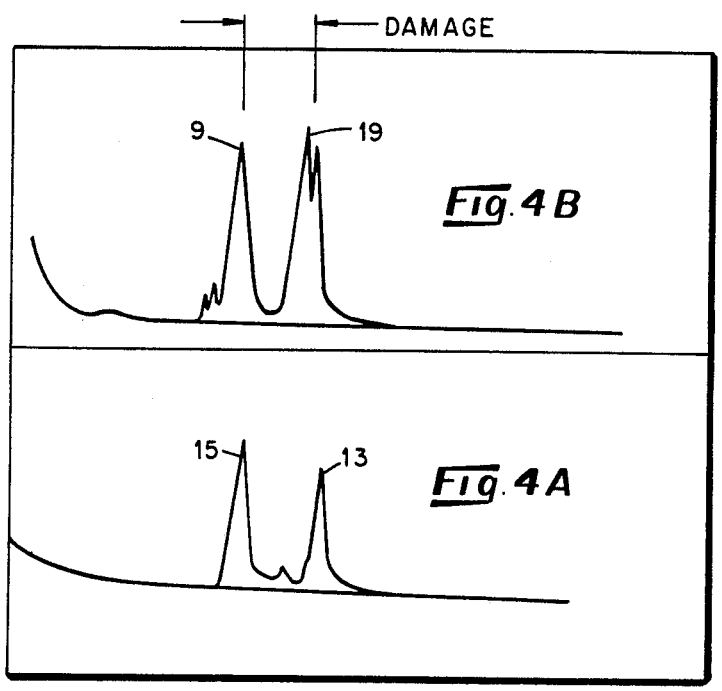
FIGS. 4A and 4B represent the spectra obtained from the patient's unburned thigh and burned thigh, respectively.

For clarity, FIGS. 2–4 do not show a "main bang" signal which is part of the typical ultrasonic reflection spectrum and is displaced to the left of the first signal shown.

DESCRIPTION OF THE PREFERRED EMBODIMENT

Our method is directed to the measurement of the depth of skin burns in human or other animal tissue. The method is based on our finding that the acoustical impedance of burned tissue differs sufficiently from that of live tissue to permit reflection of ultrasonic waves at the interface between the burn and the underlying unburned (live) tissue. As herein, the terms "ultrasound" and "ultrasonic waves" refer to sound having a frequency above 20 KHz (kilohertz); "acoustic impedance" is defined as the density of the transmitting medium multiplied by the velocity of sound in the medium; "reflection coefficient" refers to the fraction of the incident sound power that is reflected from an interface of two media.

Figure 1:
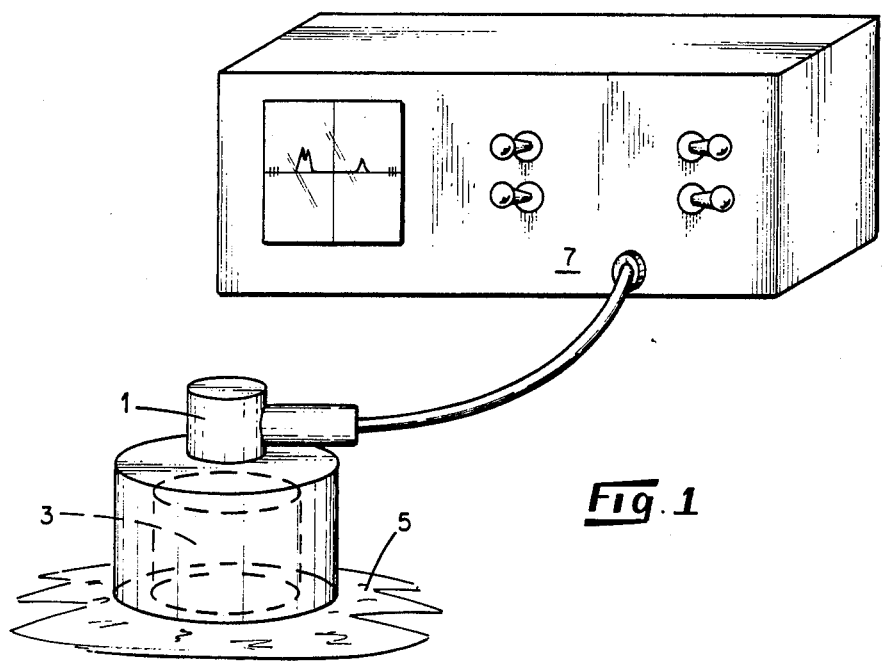
FIG. 1 is a schematic diagram of apparatus for determining burn depth in accordance with this invention.

Referring to FIG. 1, our method can be conducted with relatively simple and generally conventional apparatus. In the illustrated arrangement, a standard piezoelectric transducer 1 for transmitting and receiving ultrasonic vibrations is coupled, through an ultrasonic delay line 3, to the surface of a burn 5 in animal tissue. The delay line 3 both supports the transducer and contains a coupling gel having an acoustical impedance approximating but not exactly equaling that of soft tissue of the kind in which the burn has occurred. Matching these impedances increases the power transfer between the transducer and the tissue under examination.

The transducer 1 is mounted with its lower face substantially parallel to the gel-to-burn interface, so that the ultrasound transmitted to the interface is essentially normal to it—i.e., is within about 12° of the perpendicular of the interface. This ensures that the transducer detects a maximum amount of the reflected ultrasound. The delay line 3 is designed to provide a selected fixed spacing between the lower face of the transducer and the gel-to-burn interface. This provides some delay, or separation, between the "main bang" signal (resulting from the transducer detecting its own vibrations) and the first refected signal (reflected from the gel-to-burn interface). Providing such a delay facilitates subsequent interpretation of the first reflected signal.

Coupled to the electrodes of the transducer 1 is any suitable circuitry 7 for (a) exciting the transducer to emit ultrasound having a peak frequency or predominant frequency, in the range of from about 0.5 to 40 megahertz and (b) generating an output indicative of the time spacing of electric output signals generated by the transducer. The circuitry may, for example, be a commercially available echoencephaloscope providing a video display of the time relationship of transducer output signals, which display is referred to herein as a "video display" or alternatively, as an "ultrasonic-reflection spectrum." Conventional ultrasonic instrumentation used for non-destructive testing also can be readily modified for this use.

Briefly, our method is conducted as follows with the apparatus illustrated in FIG. 1. The delay line 1 is checked to make sure that it is free of air bubbles, after which the delay line 1 transducer assembly is positioned gently on the burn. The circuitry then is energized to excite the transducer 1 and to display the resulting ultrasonic reflection spectrum. FIG. 2 is an idealized representation of the reflection spectrum obtained with a second-degree burn, the "main bang" signal not being shown. As illustrated, the spectrum includes a first reflection signal 9, produced by the gel-to-burn interface. Because of the epidermis-dermis interface and the relatively rough surface of the burn, the signal is multipeaked. A second distinct reflection signal 11 is produced by reflection from the burn-to-unburned-tissue interface. The spacing between the leading edges of the signal 9 and the signal 11 is proportional to the thickness, or depth, of the burn. Thus, with a suitably calibrated graticule the depth of the burn can be determined by inspection of the display. Still referring to FIG. 2, a third reflection signal 13 represents the tissue-to-fat-layer interface. In this example, the signal 13 is well displaced from the signal 11, indicating that the burn under inspection does not extend to the subcutaneous fat layer—i.e., is not a third-degree burn. The spectrum shown in FIG. 2 was obtained from an actual burn; as determined by inspection of the video display, the depth of the burn was 1.4 mm. Additional details of our method are presented in the following examples.

EXAMPLE I

Depth-of-burn measurements in both porcine and human tissue were conducted in accordance with this invention. In these tests the transducer 1 was a standard highly damped broad-band transducer of the piezoelectric ceramic type [Model M110 (peak frequency: 5 MHz), manufactured by Panametrics, Inc.]. The ultrasound output from the transducer comprised pulses having a duration of about 200 n sec and consisting of a large number of component frequencies centered about the peak frequency; the substantial components had frequencies in the range of about 0–8 MHz. The delay line 3 comprised a plastic disk, to the underside of which was cemented an annular rubber grommet containing a standard water-soluble coupling gel produced by Aquasonic, Inc. The area of the coupling gel in contact with the tissue under inspection was about 8 $cm^2$. The delay line provided a spacing of 8 mm between the transducer and the gel-to-tissueinterface. The transducer was mounted on the plastic disk so that the lower face of the transducer was essentially parallel to the surface of the tissue. The circuitry for exciting the transducer and determining the time relationship of transducer output signals was a commercial echoencephaloscope (Model 7215B, manufactured by Hewlett-Packard Corporation). Minor straightforward modifications were made in this instrument to (1) ensure that the voltage pulses applied to the transducer had a half-width of 70 nanoseconds and a peak magnitude of -350 volts (frequency, ∼ 500/sec.); (2) reduce the oscilloscope display scale to one mm per division of the fraticule; and (3) narrow the reflection-signal peaks appearing in the video display.

The equipment just described was employed to make depth measurements of a burn on the dorsal surface of a 5-month-old pig and to make corresponding measurements of unburned tissue adjacent to the burn. The measurement of the unburned tissue was made first, at which time the gain control for adjusting the video reflection signals was set so that the signals respectively representing the gel-to-tissue interface and the tissue-to-fat-layer interface were clearly defined. The measurement of the burned tissue then was made at the same gain setting. FIG. 3 compares the ultrasonic reflection spectra for the unburned ("normal") tissue, the fresh burn, and the burn on subsequent days. Referring to the legends of the postburn spectra, "3 days postburn" refers to a display obtained 3 days after the fresh-burn measurement, and so on.

Referring to FIG. 3, the "normal" spectrum is characteristic of displays representing unburned tissue. That is, the normal spectrum typically includes two prominent, separated signals. The first signal 15 includes peaks representing the gel-to-epidermis interface and the epidermis-to-dermis interface, whereas the second signal 13 comprises a single peak representing the dermis-to-fat-layer interface. Comparing the fresh-burn spectrum to the normal spectrum, the initial reflection peak 9 in the burn spectrum is noticeably higher and more complex. That is, the fresh burn had a higher reflection coefficient than the unburned tissue. Furthermore, a new and distinct peak 11 is displayed as a result of reflection from the newly generated burn-to-unburned-dermis interface. A third distinct peak 13 indicates the position of the unburned-tissue-to-fat interface. As shown in the sequential postburn spectra, the new peak 11 became more distinct by the third day after the fresh-burn measurement and remained prominent until depth measurements were terminated. It is evident from the postburn spectra (especially for the third-day postburn and those thereafter) that the burn is a second-degree burn, since the peaks 11 and 13 clearly are separate. In other words, the spacing between these peaks shows that the burn does not extend to the fat layer. As determined from inspection of the video displays, the depth of the burn was judged to be ∼ 1420 $\mu m$. This determination was supported by examination of histological sections, which showed a substantial tinctorial interface at this depth.

EXAMPLE II

In another series of tests, the depths of less severe burns in porcine skin were determined ultrasonically in accordance with out method. The specimens were stained by a technique rendering the burn-destroyed tissue purple and the subcutaneous fat layer a lighter shade of pink. For purposes of comparison, the depths of the burns were measured with an ocular micrometer. The depths determined by the two measuring techniques agreed within 2%—i.e., the depth was determined to be ∼ 1.42 mm as measured ultransonically and 1.39 ± 0.09 mm as measured microscopically. The ultrasonic reflection spectra indicated that the burns were of the second degree, and this was confirmed by microscopic biology. The subsequent history of the burns supported the ultrasonic determination that they were of the second degree. That is, within 2 weeks the burns had healed completely, with negligible eschar formation.

Ultrasonic tests conducted with superficial burns produced distinctive reflection spectra in which the signal representing the burn-to-unburned-tissue interface is not spaced from the signal representing the coupling-medium-to-burned-tissue interface but rather is merged with the same.

EXAMPLE III

Our method as described above has been used to determine the character and depth of a thigh burn sustained by an industrial employee. FIG. 4B is the video display for the burn. FIG. 4A is the display, obtained under corresponding conditions, for the unburned thigh of the patient. The "normal" display (FIG. 4A) exhibits the usual two prominent signals: peak 15 produced by the gel-to-skin interface and peak 13 produced by the dermis-to-fat interface. Comparison with FIG. 4B shows that in the display obtained from the burn the initial peak 9 is characteristically higher and more complex. Also, the normal dermis-to-fat peak 13 (FIG. 4A) has been masked by a higher and broader peak 19 produced by the burn-to-unburned-tissue interface. That is, the dermis-to-fat peak has been masked by a burn-to-fat peak, indicating that the burn is of the third degree. In many instances, at least, our method can be used to identify third-degree burns relatively early (conservatively, within 3 or 4 days after occurrence) as compared with the roughly three-week delay required by the customary practice of waiting for spontaneous separation of the dead tissue. Ultrasonic reflection spectra also are useful in the indentification of deep dermal burns, in which instance the burn-to-unburned-tissue peak appears between the initial peak 9 and the dermis-to-fat peak 13.

Referring more generally to our invention, it will be apparent to those versed in the art that our method is not limited to use of the particular equipment referred to above in connections with FIG. 1. For instance, any suitable acoustic-to-electric transducer may be employed to transmit and detect the ultrasound. We prefer to use highly damped, broad-band transducers which are excited by very narrow voltage pulses, because the ultrasonic pulses from such transducers are of short duration and comprise a large number of component frequencies centered about a peak frequency. For example, ultrasonic pulses having a peak frequency of 5 MHz may have substantial frequency components in the range of from about 0 to 8 MHz; the corresponding range for a 20 MHz transducer might be from about 0 to 25 MHz. The higher-frequency components have shorter wavelengths, and thus greater resolving power, than the ultrasound at the peak frequency; consequently, interfaces smaller than the wavelength corresponding to the peak frequency can be resolved. However, the resolution advantage of a relatively high-frequency broadband transducer is off set to an extent by the proportionally larger attenuation of high-frequency ultrasound. Given a particular application of our method, it would be well within the skill of the art to select a transducer (e.g., piezoelectric, magnetorestrictive, electromagnetic; broad-band, narrow-band, single-frequency) having the most suitable characteristics.

Our method may be practiced with various types of delay lines, coupling media, circuits for exciting transducers, and circuits for generating from reflected ultrasonic waves an output signal indicative of the time spacing therebetween. For example, the delay line may comprise a plastic tube, a water bath, or a gel-filled cuplike container. If desired, the burn-contacting end of the delay line may be closed by a very thin membrane, such as rubber or a thermoplastic-resin film; such a membrane is considered herein to be part of the coupling medium. Various coupling media have an acoustic impedance approximately equal to that of soft tissue—as, for example, glycerine, water, and saline solution. Referring to the delay line, only routine testing would be required to determine what spacing provides a satisfactory between the main-bang signal and the signal generated from the first reflected ultrasonic waves. In general, a spacing in the range of from about 5 to 10 mm is effective. Various commercial devices can be substituted for the particular echoencephaloscope referred to previously. For instance, given the teaching herein, commercial instruments such as the following could be readily adapted for this purpose by one of ordinary skill in the art: Immerscope II ultrasonic inspection system, manufactured by Tektran, Inc., and The USIP II ultrasonic flow detector, manufactured by Krautkramer, Inc.

As mentioned previously, our method includes the steps of generating electrical signals separated by a time interval proportional to the distance between the coupling-medium-to-burn surface interface and the burn-to-unburned-tissue interface and then determining the depth of the burn from those signals. The term "burn-to-unburned-tissue interface" is used herein to refer to an interface between the burn and the fat layer and also to refer to an interface between the burn and the dermis or epidermis. As indicated, the "determining" operation may comprise generating a suitably calibrated video display, or, if desired, comparing the video display for a burn with the corresponding display for an unburned-tissue control. Again, the determining operation may comprise employing conventional computing means to convert the above-mentioned time interval into a numerical display of the burn thickness, in accordance with the relation $S = vi/2$, where $S$ is thickness, $v$ is the velocity of sound in soft tissue ($\sim$ 1540 m/sec), and $i$ is the length of the time interval (i.e., the total pulse-travel time). The determining operation also includes the use of an electronic comparator or the like to compare the above-mentioned time interval for a burn with the corresponding interval for an unburned-tissue control in order to generate signals indicating whether the burn is of the second or third degree. Again, the determination may comprise spectrum analysis of the ultrasonic reflection spectra produced as described. By "spectrum analysis" is meant the electronic analyzation of ultransonic reflection spectra into component frequencies to determine burn thickness. Again, the burn thickness may be determined by ultrasonic beam-scanning techniques, as by scanning the transducer over the surface of the burn and displaying the transducer output on a screen through the use of a modern gray-scale or color-scan converter. Other ways of conducting the determining operation will be apparent to those versed in the art.

What is claimed is:
1. The method of determining the depth of a skin burn in animal tissue, said method comprising:
   acoustically coupling an electric-to-acoustic transducer to the surface of said burn through an intervening layer of a coupling medium whose acoustical impedance approximates that of said tissue,
   electrically exciting the transducer to (a) transmit ultrasonic pulses having a peak frequency in the range of about 0.5 to 40 megahertz inwardly through said burn and (b) generate, from resulting reflected ultrasonic pulses, electrical signals separated by a time interval proportional to the distance between the coupling-medium-to-burn surface in- terface and the burn-to-unburned tissue interface, and determining the depth of said burn from said signals.

2. The method of claim 1 wherein the ultrasonic waves produced by said transducer are discrete pulses having a width in the range of from about 0.1 to 1 microsecond.

3. The method of claim 1 wherein said transducer is a piezoelectric transducer.

4. The method of claim 1 wherein said coupling medium is one of a gel and a liquid.

5. The method of claim 1 wherein said intervening layer has a thickness in the range of from about 5 to 10 mm.

6. The method of claim 1 wherein the determining operation comprises generating a video display of said signals.

7. The method of determining the depth of a skin burn in animal tissue, said method comprising:

acoustically coupling an electric-to-acoustic transducer to the surface of said burn through an intervening layer of a coupling medium whose acoustical impedance approximates that of said tissue, p1 electrically exciting the transducer to (a) transmit discrete ultrasonic pulses having a peak frequency in the range of about 0.5 to 40 megahertz and a width in the range of from about 0.1 to 1 microsecond inwardly through said burn and (b) generate electrical signals respectively produced by ultrasonic reflection of said pulses from the coupling-medium-to-burn-surface interface and the burn-to-unburned-tissue interface, and determining the depth of said burn from said signals.

8. The method of claim 7 wherein the determining operation comprises computing the burn depth from the equation $S = vi/2$, where $S$ is burn depth, $v$ is the velocity of sound in said tissue, and $i$ is the total travel time of the typical ultrasonic pulse in said tissue.

9. The method of claim 7 wherein the determining operation comprises comparing said electrical signals with electrical signals similarly produced from corresponding but unburned animal tissue.

10. The method of claim 9 wherein the electrical signals produced from the burned tissue and the electrical signals produced from the unburned tissue are respectively converted to video displays.

* * * * *